US00PP35448P2

(12) United States Plant Patent
Malinowski et al.

(10) Patent No.: US PP35,448 P2
(45) Date of Patent: Oct. 31, 2023

(54) ***HIBISCUS* PLANT NAMED '14-0704-02'**

(50) Latin Name: *Hibiscus rosa-sinensis*
Varietal Denomination: 14-0704-02

(71) Applicant: The Texas A&M University System, College Station, TX (US)

(72) Inventors: Dariusz Malinowski, Vernon, TX (US); Andrzej Klimowski, Wloclawek (PL); Robert Steven Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 18/105,056

(22) Filed: Feb. 2, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

(56) References Cited

PUBLICATIONS

UPOV—International Union for the Protection of New Varieties of Plants; "Guidance for the Preparation of Laws on the 1991 Act of the UPOV Convention," UPOV/INF/6/5, Apr. 6, 2017. (4 pages total).*

* cited by examiner

*Primary Examiner* — Susan McCormick Ewoldt
(74) *Attorney, Agent, or Firm* — The Webb Law Firm

(57) ABSTRACT

A new and distinct *Hibiscus* plant having ruby-red colored flowers and a compact growth habit.

2 Drawing Sheets

Botanical classification: *Hibiscus rosa-sinensis.*
Varietal denomination: '14-0704-02'.

BACKGROUND OF THE INVENTION

The present invention comprises a new and distinct *Hibiscus* plant having the varietal name '14-0704-02'. The new variety is the result of a planned breeding program with the purposes of developing tropical *Hibiscus rosa-sinensis* plants with unique flower colors and a compact growth habit. '14-0704-02' is the result of a cross conducted in Vernon, Tex. between two unnamed and unpatented *Hibiscus rosa-sinensis* varieties. The new variety was selected in June of 2015 in Vernon, Tex. and the first asexual reproduction of the new variety was conducted by cuttings in April of 2016 in Vernon, Tex. '14-0704-02' has been trial and field tested and has been found to retain its distinctive characteristics and remain true to type through successive propagations. The present invention has not been evaluated under all possible environmental conditions. The phenotype may vary with variations in environment without a change in the genotype of the plant.

'14-0704-02' is similar to its female parent in having a compact growth habit. However, the female parent of '14-0704-02' has flat, dual-colored flowers that are pinkish-red in the center with yellow petal edges, while '14-0704-02' has slightly layered petals and ruby-red colored flowers. Further, the female parent has an orange colored stigma and the stigma of '14-0704-02' is ruby-red in color. '14-0704-02' is similar to its male parent in flower shape and having a compact growth habit. However, the male parent has a bright red flower color, while '14-0704-02' has a ruby-red flower color.

When '14-0704-02' is compared to *Hibiscus rosa-sinensis* variety "Rio Clara" 'Ruby Red' (unpatented), both varieties have a deep red flower color, similar flower shape, and glossy leaves. However, '14-0704-02' has a less compact growth habit than "Rio Clara" 'Ruby Red'.

The following traits distinguish '14-0704-02' as a new and distinct cultivar from other *Hibiscus* varieties known to the breeder:

1. Ruby-red flower color;
2. Compact growth habit;
3. Increased resistance to white fly (*Trialeurodes vaporariorum*) and bacterial leaf spot (*Pseudomonas cichorii*); and
4. Dark green colored and glossy leaves.

DESCRIPTION OF THE DRAWINGS

The accompanying photographic images illustrate the new variety at approximately one year of age, with the colors being as nearly true as is possible with color illustrations of this type.

DESCRIPTION OF THE PLANT

Figure 1:
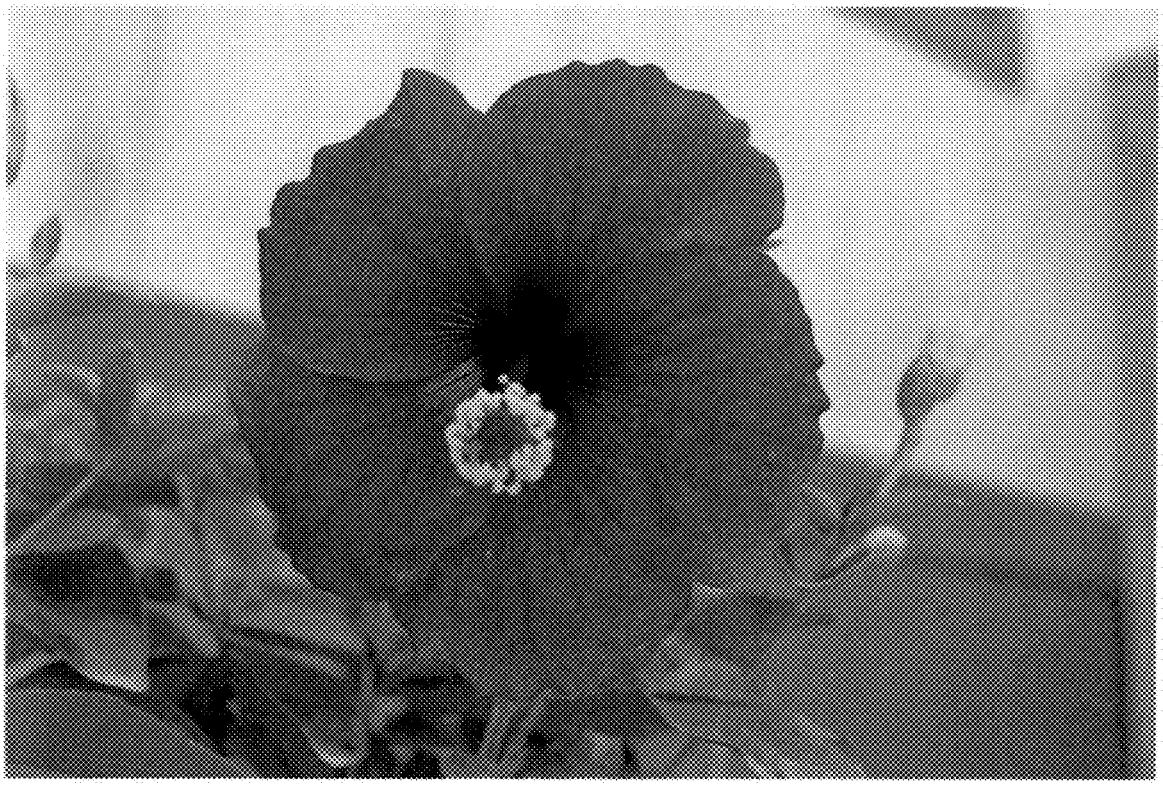
FIG. 1 illustrates a close-up view of a flower of the new variety.
Figure 2:
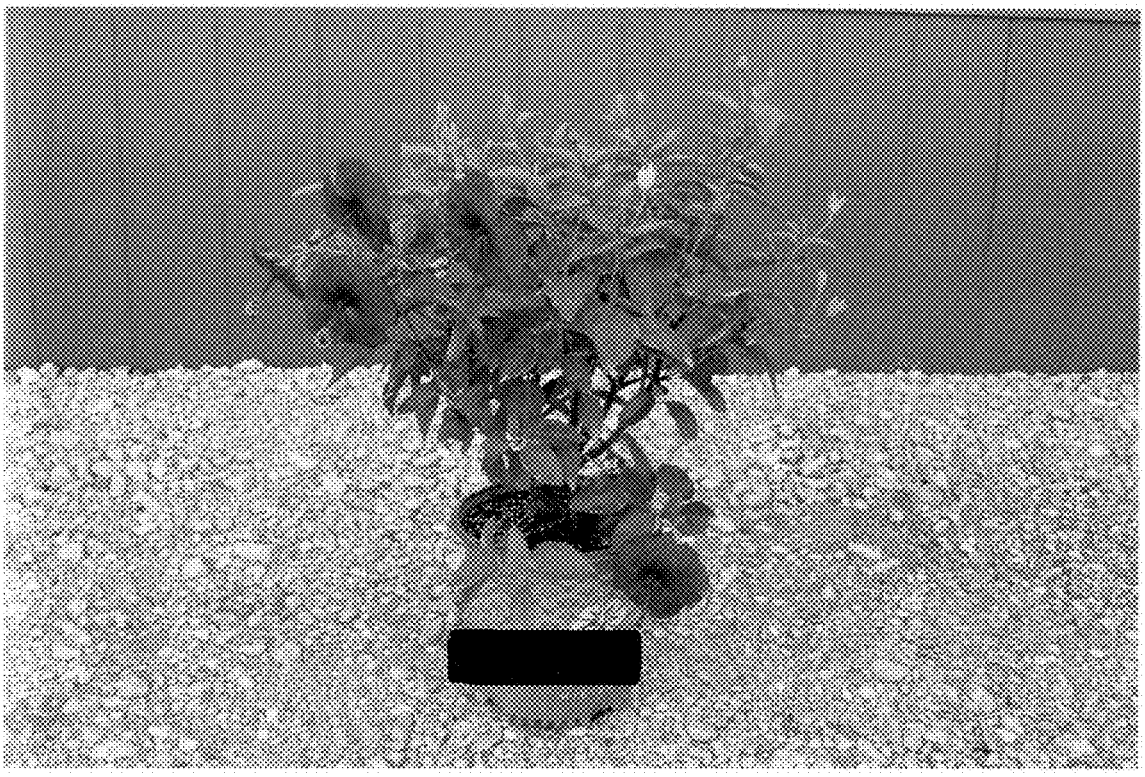
FIG. 2 illustrates an entire plant of the new variety.

The following detailed description sets forth the characteristics of the new variety at one year of age. The plants were primarily grown in 2 gallon containers in cool season heated greenhouses with a minimum temperature of approximately 13° C. and about 30% light shade in the summer months. The color readings and measurements were taken in Grand Saline, Tex. indoors under fluorescent lights with natural light from a window nearby. Color references are primarily to The 1995 R.H.S. Colour Chart of The Royal Horticultural Society of London, 3$^{nd}$ Edition, except where general color terms are used.

PLANT

Time to initiate roots: About 12 days at an average of 24° C.
Time to develop roots: About 50 days at an average of 21-24° C.
Time to produce a finished flowering plant from a rooted cutting: About 12-16 weeks in a 1 gallon/20.0 cm diameter container.
Specific disease/pest resistance: Resistance to whitefly (*Trialeurodes vaporariorum*) and bacterial leaf spot (*Pseudomonas cichorii*).
Heat/cold tolerance: Thrives above 13° C., but expires at temperatures of 0° C. and below.
Drought tolerance: Moderate to none.
Plant:
*Type.*—Tropical, ornamental shrub.
*Habit.*—Compact; upright; well-branched.
*Height.*—50.8 cm from the top of the container to the top of the plant.
*Spread.*—58.4 cm.
*Vigor.*—High.
*Rooting.*—Coarse and well-branched.
Stem:
*Number per plant.*—8.
*Length.*—37.5-40.0 cm.
*Width.*—0.6-1.3 cm.
*Texture.*—Immature: Slightly coarse, but smooth. Mature: Very coarse with a heavy bark-like texture.
*Strength.*—Moderately firm.
*Branch arrangement.*—Alternate.
*Branch number.*—27.
*Internode length.*—2.5-4.3 cm.
*Color.*—Immature: 144B. Mature: 200D.
*Stipules.*—Number per node: 2. Shape: Spinose. Length: 9.0 mm. Width: 1.0 mm. Surface texture: Smooth. Apex: Acute. Base: Linear. Margin: Entire. Color: 143C.
Foliage:
*Arrangement.*—Alternate.
*Size of leaf.*—Length: 9.8 cm. Width: 6.8 cm.
*Shape of leaf* (*generally*).—Obovate.
*Shape of apex.*—Acute.
*Shape of base.*—Cordate.
*Texture.*—Upper surface: Slick and waxy with a slight texture from venation. Lower surface: Relatively smooth with a heavier vein texture.
*Margin type.*—Slightly serrated.
*Color.*—Young leaves: Upper surface: 144A. Lower surface: 143A. Mature leaves: Upper surface: 137B. Lower surface: 146A.
*Veins.*—Venation type: Palmate. Color: Upper surface: 137A. Lower surface: 138A.
*Petiole.*—Length: 3.2 cm. Diameter: 3.0 mm. Texture: Smooth. Color: 143A.

FLOWERS

Buds (described approximately 2 days from opening):
*Shape.*—Oval.
*Diameter.*—1.6 cm.
*Length.*—4.1 cm.
*Color.*—178B.
Natural flowering season: Year round in Grand Saline, Tex.
Flower type and habit: Single with slightly overlapping petals.
Fragrance: None.
Flowers:
*Number per stem.*—1.
*Overall depth.*—1.3 cm.
*Overall diameter.*—12.1 cm.
*Shape.*—Rotate.
*Lastingness.*—1 day on the plant.
*Petals.*—Number: 5. Arrangement: Simple. Length: 7.6 cm. Width: 5.7 cm. Shape: Ovate. Apex: Obtuse Base: Acute Margin: Entire. Texture/appearance: Upper surface: Very smooth and velvety. Lower surface: Smooth with venation texture. Color: Upper surface: 46B with a 187B eye. Lower surface: 45A. Fully opened: Upper surface: 51B. Lower surface: 181D.
*Calyx.*—Form: Fused. Overall length: 3.0 cm. Overall diameter: 1.6 cm. Sepals/calyx lobes: Number: 5. Shape: Lanceolate. Apex: Acute. Margin: Entire. Texture: Slightly rough. Color: Outer surface: 144A. Inner surface: 146D.
Epicalyx:
*Length.*—12.0 mm.
*Width.*—3.0 mm.
*Texture.*—Very smooth inside and more textured outside.
*Color.*—143B.
*Sepal-like bracts.*—Not present.
*Bracts.*—Not present.
*Peduncle.*—Length: 11.0 mm. Diameter: 3.0 mm. Strength: Firm, with some flexibility. Angle: Acute. Texture: Slightly textured. Color: 144A.
Reproductive organs:
*Gynoecium.*—Pistils: Number: 1. Length: 8.3 cm. Stigma: Number: 5. Shape: Round. Length: 7.0 mm. Diameter: 6.0 mm. Color: 53A. Style: Length: 7.3 cm. Width: 4.0 mm. Color: 53B. Ovary: Shape: Ovate. Length: 12.0 mm. Width: 8.0 mm. Color: 4D.
*Androecium.*—Stamens: Number: 84. Position: Below the stigma on the style. Anther: Shape: U-shaped. Diameter: 1.0 mm. Color: 14A. Filament: Length: 6.0 mm. Width: 1.0 mm. Color: 64A. Pollen: Color: 17B. Amount (generally): Abundant.

SEEDS

Seeds: None produced.

I claim:

1. A new and distinct variety of *Hibiscus* plant named '14-0704-02', substantially as illustrated and described herein.

* * * * *